(12) United States Patent
Miao et al.

(10) Patent No.: US 10,750,960 B2
(45) Date of Patent: Aug. 25, 2020

(54) PASSIVE ARRYTHMIAS DETECTION BASED ON PHOTOPLETHYSMOGRAM (PPG) INTER-BEAT INTERVALS AND MORPHOLOGY

(71) Applicant: Samsung Electronics Co., Ltd., Suwon-si, Gyeonggi-do (KR)

(72) Inventors: Lifeng Miao, San Jose, CA (US); Manman Zhang, Cupertino, CA (US); Matthew Wiggins, San Jose, CA (US)

(73) Assignee: Samsung Electronics Co., Ltd. (KR)

(*) Notice: Subject to any disclaimer, the term of this patent is extended or adjusted under 35 U.S.C. 154(b) by 177 days.

(21) Appl. No.: 15/994,495

(22) Filed: May 31, 2018

(65) Prior Publication Data

US 2018/0279891 A1    Oct. 4, 2018

Related U.S. Application Data

(63) Continuation-in-part of application No. 15/145,356, filed on May 3, 2016, now Pat. No. 10,390,758.

(Continued)

(51) Int. Cl.
*A61B 5/024* (2006.01)
*A61B 5/00* (2006.01)
(Continued)

(52) U.S. Cl.
CPC ...... *A61B 5/02416* (2013.01); *A61B 5/02405* (2013.01); *A61B 5/02438* (2013.01); *A61B 5/681* (2013.01); *A61B 5/6824* (2013.01); *A61B 5/046* (2013.01); *A61B 5/0468* (2013.01); *A61B 5/721* (2013.01); *A61B 5/725* (2013.01); *A61B 5/7285* (2013.01); *A61B 5/74* (2013.01)

(58) Field of Classification Search
None
See application file for complete search history.

(56) References Cited

U.S. PATENT DOCUMENTS 6,272,377 B1 * 8/2001 Sweeney .............. A61N 1/3622
600/515
6,516,219 B1    2/2003 Street
(Continued)

FOREIGN PATENT DOCUMENTS

KR    10-1210828 B1    12/2012

*Primary Examiner* — Brian T Gedeon
(74) *Attorney, Agent, or Firm* — Innovation Counsel LLP

(57) ABSTRACT

A method for event detection in a user-wearable device includes receiving, from a first sensor implemented in the user-wearable device, photoplethysmogram (PPG) signals; processing, at a processor, the PPG signals to obtain PPG signal samples; detecting, at the processor, beats in the PPG signal samples; dividing the PPG signal samples into PPG signal segments; extracting at least one inter-beat interval (IBI) feature in each PPG signal segment; classifying, at the processor, each PPG signal segment using the extracted IBI feature associated with the PPG signal segment and using a machine learning model; in response to the classifying, generating, at the processor, an event prediction result for the PPG signal segment based on the extracted IBI feature; and displaying the event prediction result at the user-wearable device. In another embodiment, the method further includes extracting morphology based features.

22 Claims, 10 Drawing Sheets

Related U.S. Application Data

(60) Provisional application No. 62/648,821, filed on Mar. 27, 2018.

(51) Int. Cl.
　　*A61B 5/0468*　　　(2006.01)
　　*A61B 5/046*　　　　(2006.01)

(56) References Cited

U.S. PATENT DOCUMENTS

| | | |
|---|---|---|
| 9,420,956 B2 * | 8/2016 | Gopalakrishnan ... A61B 5/0245 |
| 10,206,593 B2 * | 2/2019 | Ukil ..................... A61B 5/7221 |
| 2008/0188762 A1 * | 8/2008 | John ..................... A61B 5/0452 |
| | | 600/513 |
| 2010/0274303 A1 | 10/2010 | Bukhman |
| 2016/0120434 A1 * | 5/2016 | Park ..................... A61B 5/6832 |
| | | 600/301 |
| 2016/0360974 A1 | 12/2016 | Lange |
| 2017/0135593 A1 | 5/2017 | Huang et al. |
| 2017/0188872 A1 | 7/2017 | Hughes et al. |
| 2017/0258342 A1 | 9/2017 | Ukil et al. |

* cited by examiner

Clinimark subjects: 28
AF windows: 256
NSR windows: 48

# PASSIVE ARRYTHMIAS DETECTION BASED ON PHOTOPLETHYSMOGRAM (PPG) INTER-BEAT INTERVALS AND MORPHOLOGY

CROSS REFERENCE TO RELATED APPLICATIONS

This application claims priority to U.S. Provisional Patent Application No. 62/648,821, entitled PASSIVE ARRHYTHMIAS DETECTION BASED ON PHOTOPLETHYSMOGRAM (PPG) INTER-BEAT INTERVALS AND MORPHOLOGY, filed Mar. 27, 2018, which is incorporated herein by reference for all purposes.

This application is a continuation-in-part of U.S. patent application Ser. No. 15/145,356, entitled METHOD AND APPARATUS FOR TRIAGE AND SUBSEQUENT ESCALATION BASED ON BIOSIGNALS OR BIOMETRICS, filed May 3, 2016, which is incorporated herein by reference for all purposes.

FIELD

The present disclosure relates to a medical monitoring device and method thereof, and, in particular, to a system and method for arrhythmias detection using a wearable device.

BACKGROUND

Heart arrhythmia, also known as cardiac dysrhythmia or irregular heartbeat, is a group of conditions in which the heartbeat is irregular, too fast, or too slow. While most types of arrhythmia are not serious, some predispose a person to complications such as stroke or heart failure. Others may result in cardiac arrest. For example, Atrial Fibrillation (AFib) is one of the most common cardiac arrhythmia and the presence of AFib could potentially lead to major health risks. Traditionally, heart arrhythmia is detected by electrocardiogram (ECG) or a Hotler monitor.

ECG measurements require sophisticated detection device with multiple electrodes attached to the patient and require active human participation. Typically, ECG measurements are taken only for diagnostic purpose after the patient become symptomatic. Photoplethysmogram (PPG) has been described as an alternative to ECG in arrhythmia detection. However, some conventional PPG measurement technique for heart arrhythmia relies primarily on heart beat or heart rate detection using an average heart rate, such as a window between 5 and 20 seconds. Average heart rate variation by itself is not a reliable sign for arrhythmia.

Other PPG based methods for detecting heart arrhythmia suffer from low sensitivity and specificity. Also, some methods require a large continuous chunk of PPG signal, such as 30 seconds of continuous PPG signal to effectuate the measurement.

SUMMARY

The present disclosure discloses a device and method for arrhythmias detection substantially as shown in and/or described below, for example in connection with at least one of the figures, as set forth more completely in the claims.

These and other advantages, aspects and novel features of the present disclosure, as well as details of an illustrated embodiment thereof, will be more fully understood from the following description and drawings.

In one embodiment, a method for event detection in a user-wearable device includes receiving, from a first sensor implemented in the user-wearable device, photoplethysmogram (PPG) signals; processing, at a processor, the PPG signals to obtain PPG signal samples; detecting, at the processor, beats in the PPG signal samples; dividing the PPG signal samples into PPG signal segments; extracting at least one inter-beat interval (IBI) feature in each PPG signal segment; classifying, at the processor, each PPG signal segment using the extracted IBI feature associated with the PPG signal segment and using a machine learning model; in response to the classifying, generating, at the processor, an event prediction result for the PPG signal segment based on the extracted IBI feature; and displaying the event prediction result at the user-wearable device.

In another embodiment, a method for event detection in a user-wearable device includes receiving, from a first sensor implemented in the user-wearable device, photoplethysmogram (PPG) signals; processing, at a processor, the PPG signals to obtain PPG signal samples; detecting, at the processor beats in the PPG signal samples; dividing the PPG signal samples into PPG signal segments; extracting at least one morphology based feature in each PPG signal segment, the morphology based features be associated with statistical characteristics of the PPG signal samples or waveform characteristics of the PPG signal samples; classifying, at the processor, each PPG signal segment using the extracted morphology based feature associated with the PPG signal segment and using a machine learning model; in response to the classifying, generating, at the processor, an event prediction result based on the extracted morphology based feature; and displaying the event prediction result at the user-wearable device.

In another embodiment, an apparatus includes a sensor module comprising a first sensor configured to measure photoplethysmogram (PPG) signals; and a processor including a data processing module configured to process the PPG signals to obtain PPG signal samples, to detect beats in the PPG signal samples, and to divide the PPG signal samples into PPG signal segments; an inter-beat interval detection module configured to extract at least one inter-beat interval (IBI) feature in each PPG signal segment; a morphology detection module configured to extract at least one morphology based feature in each PPG signal segment; and a classification module configured to classify each PPG signal segment using the extracted IBI feature and the extracted morphology based feature associated with the segment and using a machine learning model, the classification module further configured to generate an event prediction result based on the extracted IBI feature and the extracted morphology based feature.

BRIEF DESCRIPTION OF THE DRAWINGS

Various embodiments of present disclosure are disclosed in the following detailed description and the accompanying drawings.

FIG. 1(a) and FIG. 1(b), illustrates an electronic device according to embodiments of the present disclosure.

DETAILED DESCRIPTION

Figure 1:
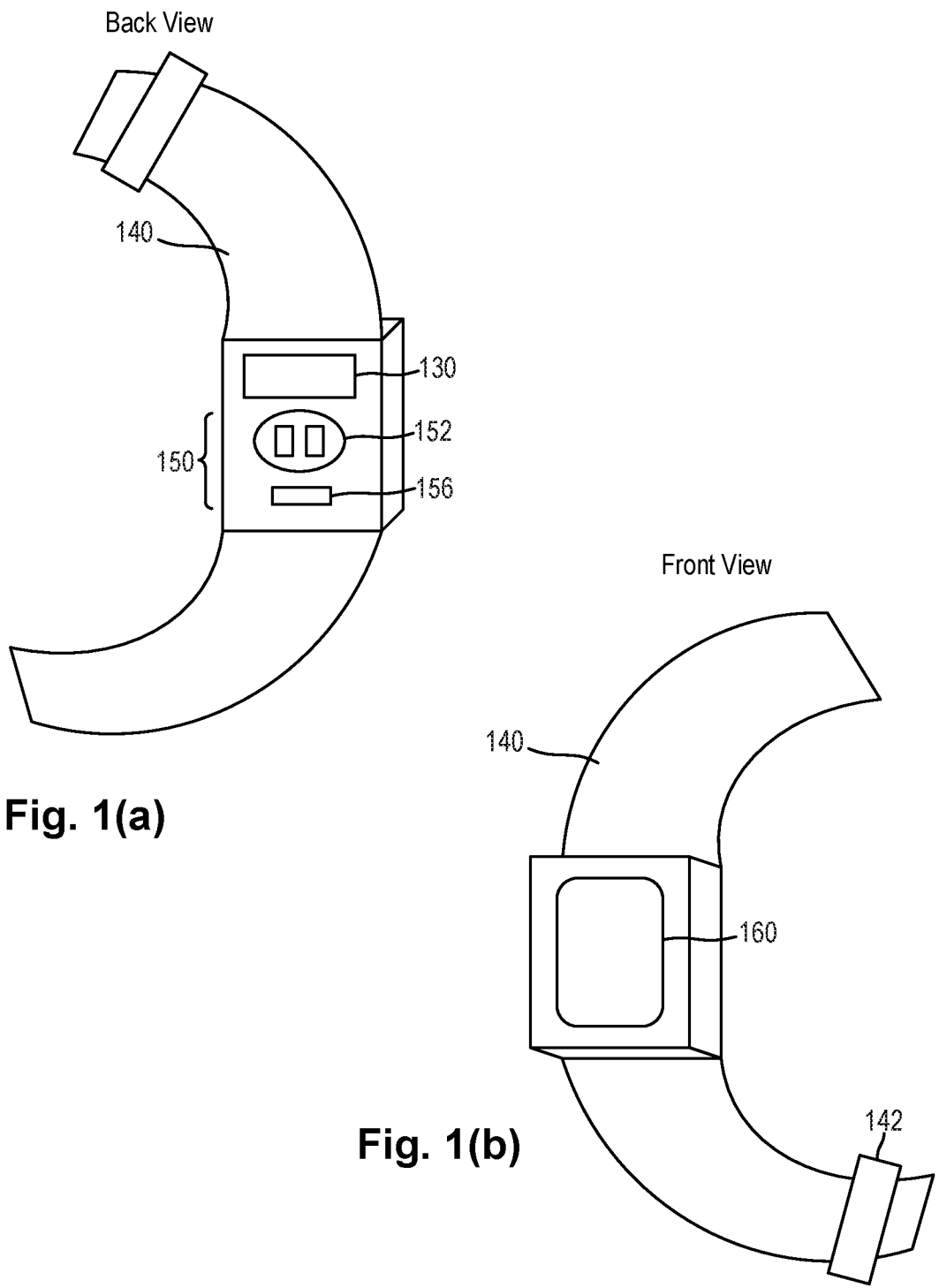
FIG. 1, which includes

Present disclosure can be implemented in numerous ways, including as a process; an apparatus; a system; a composition of matter; a computer program product embodied on a computer readable storage medium; and/or a processor, such as a hardware processor or a processor device configured to execute instructions stored on and/or provided by a memory coupled to the processor. In this specification, these implementations, or any other form that present disclosure may take, may be referred to as techniques. In general, the order of the steps of disclosed processes may be altered within the scope of present disclosure. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of present disclosure is provided below along with accompanying figures that illustrate the principles of present disclosure. Present disclosure is described in connection with such embodiments, but present disclosure is not limited to any embodiment. The scope of present disclosure is limited only by the claims and present disclosure encompasses numerous alternatives, modifications and equivalents. Numerous specific details are set forth in the following description in order to provide a thorough understanding of present disclosure. These details are provided for the purpose of example and present disclosure may be practiced according to the claims without some or all of these specific details. For the purpose of clarity, technical material that is known in the technical fields related to present disclosure has not been described in detail so that present disclosure is not unnecessarily obscured.

In embodiments of the present disclosure, an arrhythmias detection system and method implemented in a user-wearable device provides high accuracy heart arrhythmias detection using photoplethysmogram (PPG) signals by analyzing inter-beat interval (IBI) features and/or beat-by-beat morphological features of the PPG signals. In some embodiments, the arrhythmias detection system and method processes segments of the PPG signals to analyze irregularly irregular inter-beat intervals and/or beat-by-beat morphological features of a user's PPG waveform to detect arrhythmias. In one embodiment, the arrhythmias detection system and method observe the inter-beat interval (IBI) information and/or beat-by-beat morphology information in short PPG signal segments. The PPG-based arrhythmia detection system and method is configured to extract accurate arrhythmia information from the short PPG segments, including PPG signal information that are typically rejected in conventional PPG heart rate measurement methods. In some embodiments, the PPG-based arrhythmia detection system and method provides improved detection accuracy, sensitivity, and specificity over conventional heart rate based detected methods. Importantly, the PPG-based arrhythmia detection system and method enables passive and asymptomatic arrhythmia detection. That is, arrhythmia detection can be performed before a user displays or experiences symptoms indicating arrhythmia.

In particular, conventional arrhythmia detection techniques rely exclusively on the statistical distribution of interbeat intervals in the heart beats information and do not rely on morphological information that may be present in the heart beat signal. In some aspect of the present disclosure, the arrhythmias detection system and method of the present disclosure incorporates analysis of morphological feature in the PPG signals and therefore benefits from the morphological information available in the PPG signal that is also present in the physiological conditions.

In the present description, photoplethysmogram (PPG) refers to an optically obtained plethysmogram, which is a volumetric measurement of an organ. A PPG is often obtained by using a pulse oximeter which illuminates the skin and measures changes in light absorption. A conventional pulse oximeter monitors the perfusion of blood to the dermis and subcutaneous tissue of the skin as a result of the cardiac cycle where the heart pumps blood to the periphery, resulting in a pressure pulse at the skin. The change in volume caused by the pressure pulse is detected by illuminating the skin with the light from a light-emitting diode (LED) and then measuring the amount of light either transmitted or reflected to a photodiode. The advantage of PPG-based detection is that PPG signals can be easily recorded and monitored from consumer-level wearable devices with no active effort from participants. This advantage, together with affordable wearable devices and smart phones, can make passive heart arrhythmia monitoring and detection possible.

In embodiments of the present disclosure, the PPG-based arrhythmia detection system and method of the present disclosure detects cardiac or heart arrhythmia using short discrete segments of the PPG signals and performing one or more signal analyses on the short PPG signal segments. In one embodiment, the system analyzes the statistical regularity of the distribution of the inter-beat intervals of the PPG beats contained in each PPG signal segment. In another embodiment, the system analyzes morphology based features of the PPG beats contained in each PPG signal segment. In some examples, the system may analyze the statistical distribution of morphology characteristics or the similarity between morphology based features of adjacent PPG beats extracted from each PPG signal segment. In yet another embodiment, the system performs both set of analysis—that is both the inter-beat interval characteristics and the morphology features are analyzed to detect arrhythmia.

Accordingly, in some embodiments, the PPG-based arrhythmia detection system and method provides high accuracy heart arrhythmias detection by analyzing only inter-beat interval (IBI) features of the PPG signal segments, or by analyzing beat-by-beat morphological based features of the PPG signal segment. In some cases, information relating to the beat-by-beat morphological features of the PPG signal segments is added to the analysis based on the IBI features to increase the detection accuracy.

In the present description, the term "feature" as used in "IBI features" or "morphology based features" refers to both waveform shapes, waveform characteristics, waveform quality, and statistical properties or attributes, measured features or attributes, or derived features or attributes. For example, IBI features can include the statistical distribution of inter-beat intervals. In another example, morphology features can include waveform similarities between adjacent PPG beats. Morphology features can also include statistical distribution of certain morphology characteristics.

In alternate embodiments, the PPG-based arrhythmia detection system and method of the present disclosure uses electrocardiogram (ECG) signals to adjust the PPG signal to further enhance the detection accuracy. In one embodiment, the ECG signal is used to adaptively adjust the time interval of the detected beats in the IBI feature analysis. In another embodiment, the ECG signal is used to adaptively adjust the decision threshold during classification to increase the detection accuracy.

The PPG-based arrhythmia detection system and method of the present disclosure realizes many advantages over conventional arrhythmia detection methods using PPG. For example, the PPG-based arrhythmia detection system of the present disclosure is implemented such that it is able to analyze many short PPG signal segments and does not require a long continuous PPG segment. Information/features from multiple PPG signal segments, for instance 2 to 15 seconds in length, can be aggregated for statistical assessment and classification. The short PPG signal segments are much more frequently available than the 30 seconds signal segment required in some conventional systems. Second, the PPG-based arrhythmia detection system of the present disclosure provides more accurate detection over conventional systems using only average heart rate information. The PPG based arrhythmia detection system of the present disclosure uses inter-beat interval and beat-by-beat morphology features which can better represent the characteristics of arrhythmias and result in significant improvement in detection performance.

In an exemplary embodiment of the present disclosure, the PPG-based arrhythmia detection system and method is implemented in a wrist-based wearable device containing a PPG sensor. The user or subject wears the wrist-band wearable device continuously and the system provides notifications for arrhythmia detected. In some embodiments, the wrist-based wearable device includes an accelerometer which is used to determine continuously if the wearer is stationary. In one embodiment, when the user is stationary, the PPG optical sensor is activated to measure the PPG signal. The PPG signal is observed for a set of key indicators to determine if the wearer is having an arrhythmia. In alternate embodiments, the PPG optical sensor takes continuous measurement and the accelerometer provides motion indication signal to the PPG-based arrhythmia detection system. The PPG-based arrhythmia detection system processes the PPG signals and may discard portions of the PPG signals that are associated with high degree of motion which may impact the accuracy of the PPG signal.

FIG. 1, which includes FIG. 1(a) and FIG. 1(b), illustrates an electronic device according to embodiments of the present disclosure. FIG. 1(a) illustrates a back view of the electronic device and FIG. 1(b) illustrates a front view of the electronic device. Referring to FIG. 1, an electronic device 100, which may be a user-wearable device, has a display 160, a processor 130, a sensor module 150, a battery (not show), a band 140, and a clasp 142. The band 140 may be wrapped around a wrist and the user-wearable device 100 may be held on the wrist by using the clasp 142. The sensor module 150 include one or more sensors 152, 156 and a local processor 154 (not shown). The local processor 154 implements control function for the sensor module and may also perform processing or pre-processing of the sensed signals. The processor 130 implements control functions for the user-wearable device and may also perform further signal processing functions on the sensed signals. The local processor 154 or the processor 130 may also be referred to as a diagnostic processor.

Although the user-wearable device 100 may be worn on a wrist, various embodiments of the disclosure need not be so limited. The user-wearable device 100 may also be designed to be worn on other parts of the body, such as, for example, on an arm (around the forearm, the elbow, or the upper arm), on a leg, on the chest, on the head like a headband, on the throat like a "choker," and on an ear. The user-wearable device 100 may be able to communicate with other electronic devices such as, for example, a smart phone, a laptop, or various medical devices at a hospital or a doctor's office.

The display 160 may output monitored physiological signals from the user's body for viewing by the user and/or others. The physiological signals being monitored are sometimes referred to as biosignals or biometric data. The monitored biosignals may be, for example, heart (pulse) rate, pulse morphology (shape), pulse spacing (inter-beat intervals), respiration (breathing) rate, and blood pressure. The display 160 may also output instructions to the user or others in the use of the user-wearable device 100 or use of other measurement devices, as well as status and diagnostic results, for example.

The processor 130 receives the monitored or sensed signals from sensors in the sensor module 150. For example, the sensors 152, 156 acquire signals from the user's wrist when the user-wearable device 100 is worn by a user. In embodiments of the present disclosure, the sensor module 150 includes a sensor 152 being a biophysiological sensor. In one embodiment, the biophysiological sensor is a photoplethysmogram (PPG) sensor. In other embodiments, the sensor module 150 further includes a second sensor 156 being an inertial measurement sensor. In one embodiment, the inertial measurement sensor is an accelerometer. The sensor module 150 may include the processor 154 for controlling the sensors 152, 156, and also for processing the signals sensed by the sensors. For example, the processor 154 may decompose the signals monitored by the sensors 152, 156, and then reconstruct the decomposed signals. Various embodiments of the disclosure may have the processor 130 also performing the functions of the processor 154. Various embodiments of the disclosure may also have different number of sensors.

In some embodiments, the sensor 152 is a PPG sensor used to continuously or periodically monitor cardio-related physiological information, such as heart pulse rate or heart pulse shape, of a user. Meanwhile, the sensor 156 is an accelerometer used to continuously or periodically monitor motion information of a user. The sensor module 150 may include other sensors such as, for example, a thermometer for taking the user's temperature.

The user-wearable device 100 implements the PPG-based arrhythmia detection system of the present disclosure in the processor 130. In some embodiments, the PPG-based arrhythmia detection system includes a signal processing module to segment the PPG signals into short PPG signal segments and also include a machine learning network for evaluating the PPG signal segments and estimating the probability of the presence of heart arrhythmia in the monitored signal.

Figure 2:
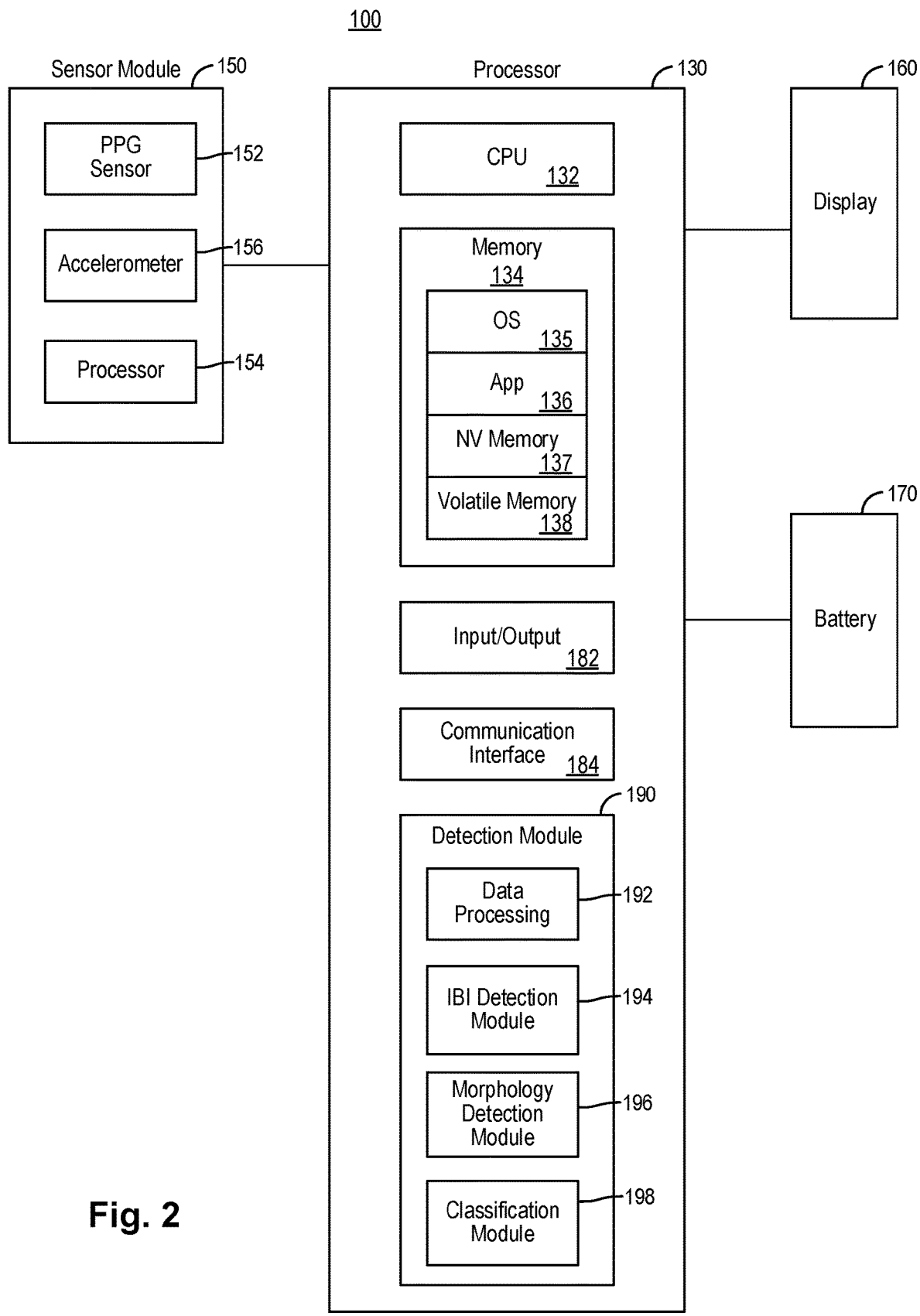
FIG. 2 illustrates a block diagram of a user-wearable device according to embodiments of the present disclosure.

FIG. 2 illustrates a block diagram of a user-wearble device according to embodiments of the present disclosure. Referring to FIG. 2, a user-wearable device 100 includes a sensor module 150, a processor 130, a display 160 and a battery 170 for providing power to the other components. The processor 130 controls the output provided on the display 160. The display 160 may also include input devices (not shown) such as, for example, buttons, dials, touch sensitive screen, and microphone.

In embodiments of the present disclosure, the sensor module 150 includes a biophysiological sensor 152 to measure a biological signal of the user. In the present embodiment, the biophysiological sensor 152 is a PPG sensor. The sensor module 150 may further include an inertial measurement sensor 156 to measure a motion signal of the user. In the present embodiment, the inertial measurement sensor 156 is an accelerometer, such as a tri-axial accelerometer. The sensor module 150 may be provided with a local processor 154 for controlling the sensors 152, 156, and also for processing the biosignals and motion signals sensed by the sensors 152, 156 respectively. In some embodiments, the signal processing operation can be implemented at the local processor 154 and/or at the processor 130. Alternately, the local processor 154 may perform part of the signal processing, such as certain signal pre-processing, and the processor 130 implements other signal processing algorithms for biometric determination or other functions. In embodiments of the present disclosure, the specific processor used to execute the biometric signal processing algorithms is not critical to the practice of the present disclosure.

In embodiments of the present disclosure, the processor 130 is configured to control the sensing operation, the sampling schedule, the signal processing operation, and device communication events and other device-specific functions in the user-wearable device. In the present embodiment, the processor 130 include a CPU 132, a memory 134, an input/output (I/O) interface 182, a communication interface 184, and a detection module 190. While the processor 130 is described as comprising these various elements, other embodiments may use other architectures where the different functionalities are grouped differently. For example, the grouping may be in different integrated circuit chips. Or the grouping may be combining different elements such as the I/O interface 182 and the communication interface 184 together.

The processor 130 incorporates the detection module 190 to perform arrhythmia detection on the sensed biosignal, such as the PPG signal. In embodiments of the present disclosure, the detection module 190 includes a data processing module 192, an IBI detection module 194, a morphology detection module 196, and a classification module 198. The signal processing module 192 is configured to perform signal preprocessing on the sensed biosignal. For example, the data processing module 192 may perform baseline removal or DC signal level removal on the sensed PPG signals. In other embodiments, the data processing module 192 may perform signal segmentation to divide the sensed PPG signals into short PPG signal segments. For example, each PPG signal segment may be between 2 to 15 seconds. Alternately, each PPG signal segment may include n number of detected beats. In one example, n is between 40 and 70. That is, each PPG signal segment can include 40 to 70 beats.

The IBI detection module 194 implements analysis of inter-beat intervals in the detected beats of the PPG signal segment. The morphology detection module 196 implements analysis of morphology based features of the detected beats of the PPG signal. In some embodiments, the detection module 190 may include either one of the IBI detection module and morphology detection module or both of the modules.

The classification module 198 implements classification of the PPG signal segments to detect the presence of arrhythmia in the PPG signal segments. The classification module 198 uses the analysis results form the IBI detection module 194 and/or the analysis results from the morphology detection module 196. The classification module 198 predicts the probability of arrhythmia presence in the PPG signal segments.

Figure 11:
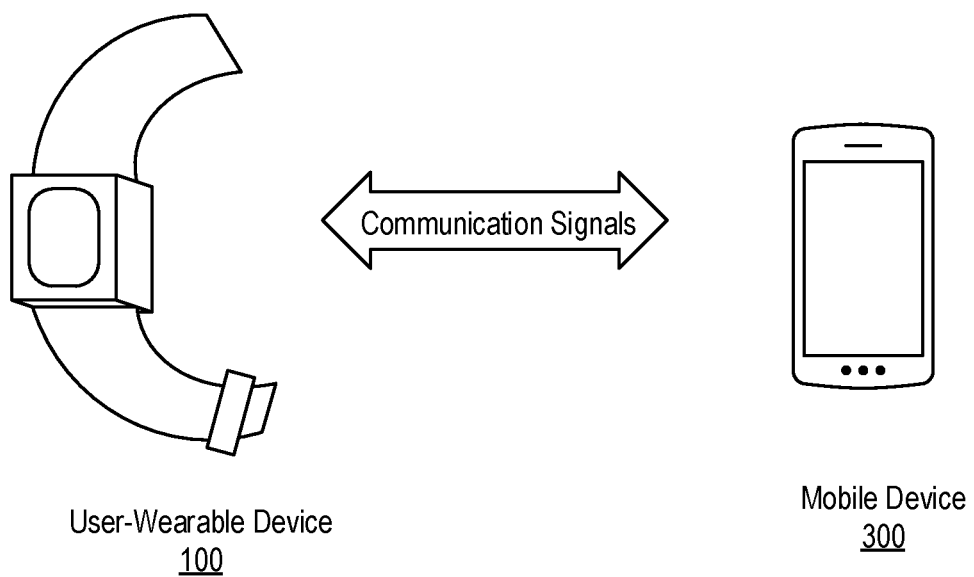
FIG. 11 illustrates a user-wearable device in communication with a mobile device in embodiments of the present disclosure.

In alternate embodiments, the arrhythmia detection system of the present disclosure may be implemented in an electronic device in communication with the user-wearable device containing the sensor module. For example, the electronic device can be a mobile device, such as a smart phone or a tablet device. The sensed PPG signals and other accompanying signals, such as motion signals, may be provided to the electronic device for signal processing and arrhythmia detection in accordance with the arrhythmia detection method of the present disclosure, as shown in FIG. 11. The electronic device may provide the detection results to be displayed on the user-wearable device.

Figure 12:
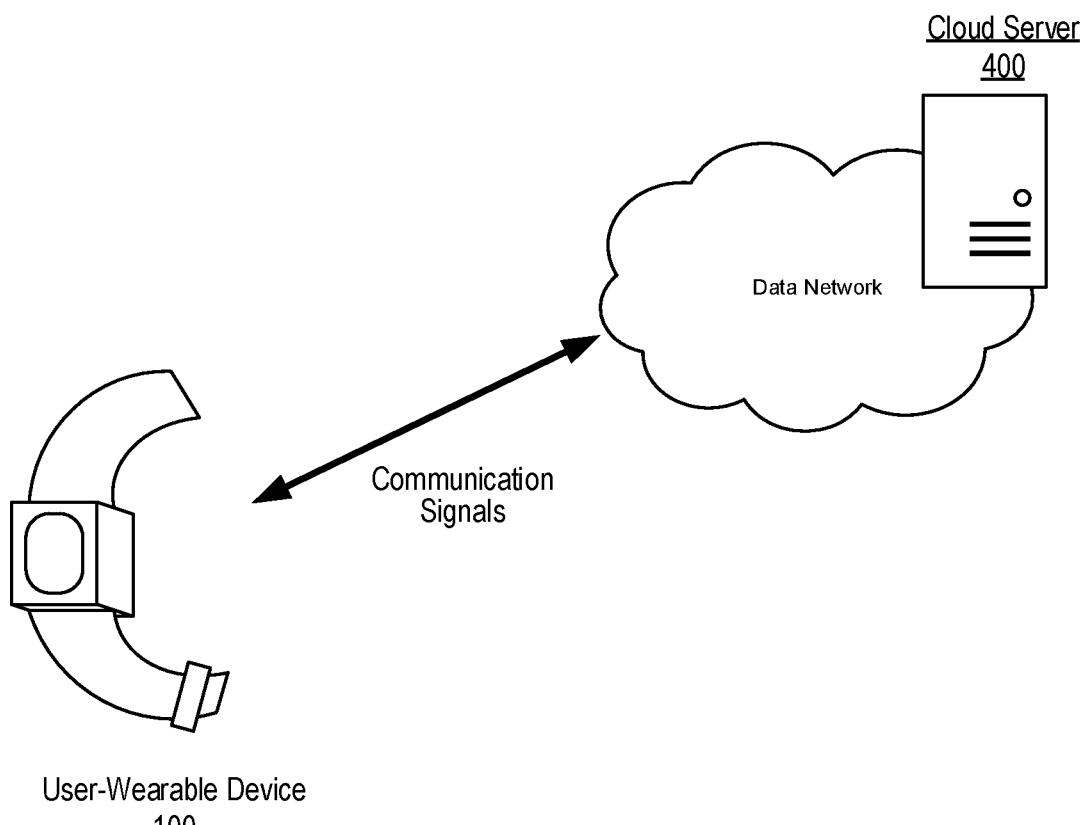
FIG. 12 illustrates a user-wearable device in communication with a cloud server in embodiments of the present disclosure.

In yet another embodiment, the arrhythmia detection system of the present disclosure may be implemented in a cloud server disposed on a data network and in communication with the user-wearable device containing the sensor module. The sensed PPG signals and other accompanying signals, such as motion signals, may be provided to the cloud server through the data network for signal processing and arrhythmia detection in accordance with the arrhythmia detection method of the present disclosure, as shown in FIG. 12. The cloud server may provide the detection results to be displayed on the user-wearable device. In the present description, a cloud server refers to a logical server that is built, hosted and delivered through a cloud computing platform over a data network, such as the Internet. For example, cloud servers possess and exhibit similar capabilities and functionality to a typical server but are accessed remotely from a cloud service provider.

Figure 3:
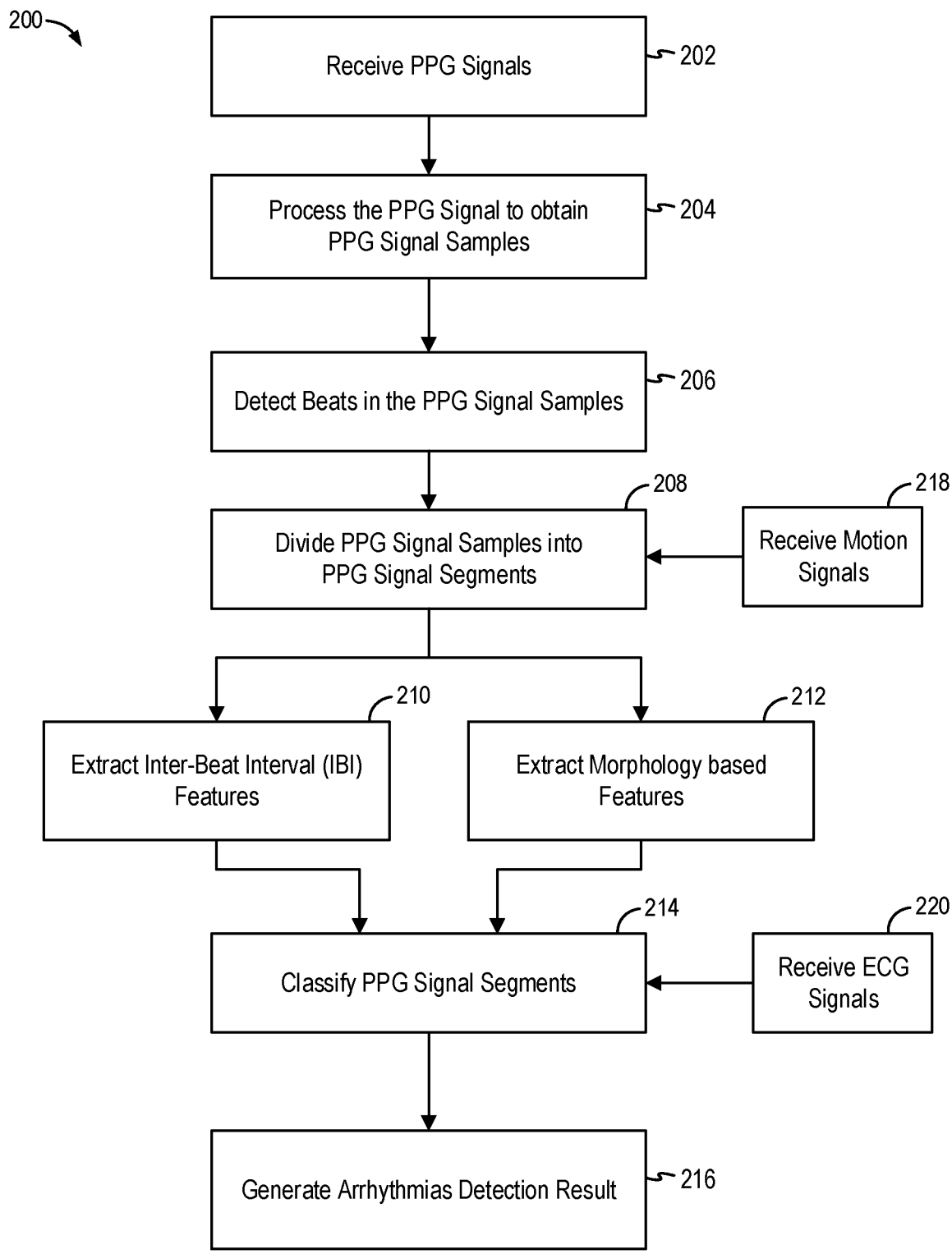
FIG. 3 is a flowchart illustrating a method for arrhythmia detection in a user wearable device in embodiments of the present disclosure.

FIG. 3 is a flowchart illustrating a method for arrhythmia detection in a user wearable device in embodiments of the present disclosure. In some embodiments, the method 200 can be implemented in a processor in a wearable device, such as the processor 130 of the user-wearable device 100 in FIGS. 1 and 2. Alternatively, the method 200 can be implemented in a mobile device in communication with the wearable device. In yet another embodiment, the method 200 can be implemented in a cloud server in communication with the wearable device. Referring to FIG. 3, the method 200 receives a channel of biosignal data signals from a first sensor implemented in the user-wearable device (202). For example, the biosignal data signals can be PPG signals. In the present embodiment, the method 200 receives raw data samples, that is, data samples that have not been processed or have been minimally processed.

At 204, the method 200 performs processing of the PPG signals to obtain PPG signal samples. In some examples, the processing of the PPG signals may include remove DC baseline signal level. In other examples, the processing can include other signal processing to enhance the signal level. As a result of the processing, PPG signal samples are generated. In one embodiment, the processing step is performed by the data processing module 192 in the detection module 190 of the processor 130 of the user-wearable device 100.

Figure 4:
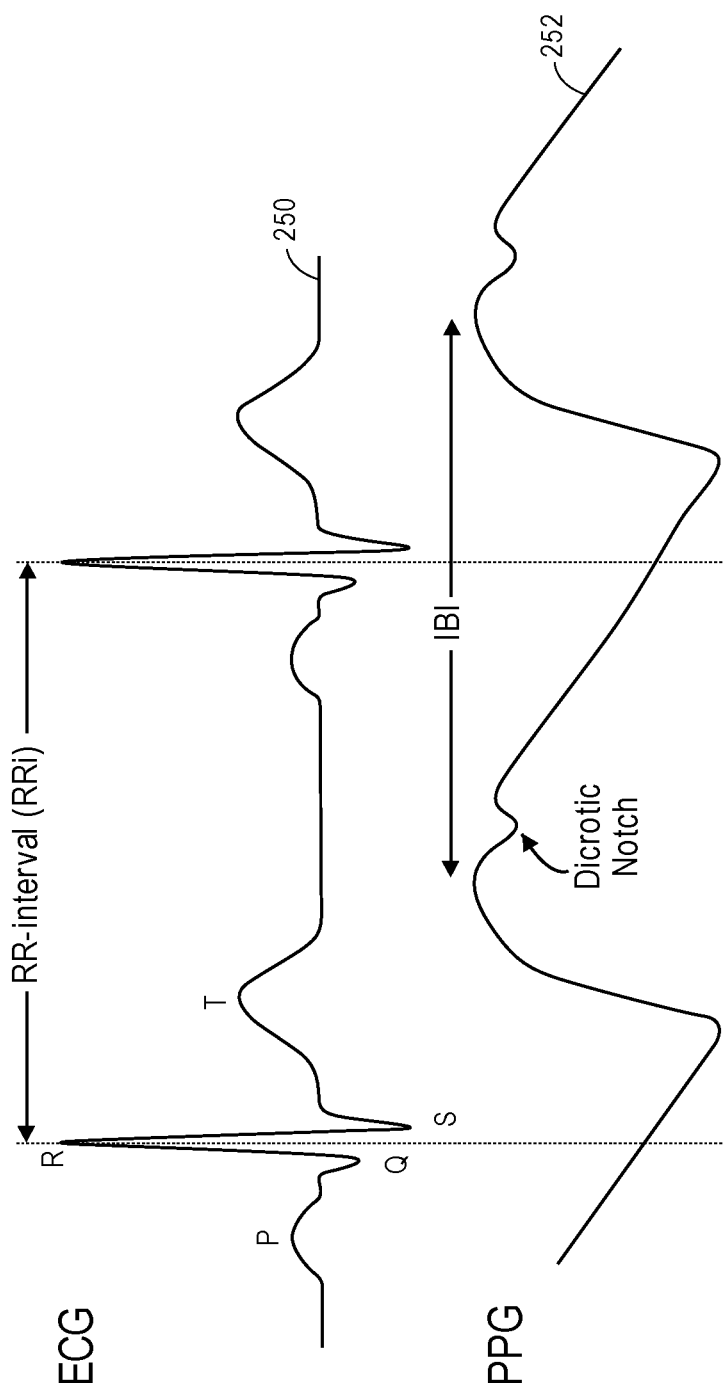
FIG. 4 illustrates exemplary signal waveforms of an ECG signal and a PPG signal.

FIG. 4 illustrates exemplary signal waveforms of an ECG signal and a PPG signal. In particular, a PPG signal for measuring cardiac rhythm or heart beat has a specific waveform profile and is different from the waveform profile of an ECG signal. Referring to FIG. 4, ECG measures the electrical activity of the heart and the ECG signal (curve 250) includes a prominent feature known as the QRS complex, which indicates the main pumping contractions of the heart. The R peak in the ECG signal is used by heart rate algorithms to measure the amount of time that occurs between each pulsing heart beat. The time duration between each R peak is referred to as the RR-interval.

Meanwhile, PPG measures the pressurized pulse of blood into the arteries of the body, which causes the arteries to swell slightly before returning to their previous state. The PPG signal is an optical signal where the amplitude of the optical signal is directly proportional to pulse pressure. The PPG signal (curve 252) includes quasi-periodic pulses, with peaks and valleys that can be used to indicate the periodicity of the signal waveform and thereby allowing the estimation of heart rate to be made. In particular, the duration between the peaks of two adjacent pulses, or the valleys of two adjacent pulses, is referred to as the inter-beat interval (IBI) which can be used as an indication of heart rate. In some cases, the PPG signal presents a dicrotic notch. A dicrotic notch is a small, downward deflection observed on the downstroke of an arterial pressure waveform. It represents the intersection of superimposed primary and reflected pressure waves in the arterial tree.

Figure 5:
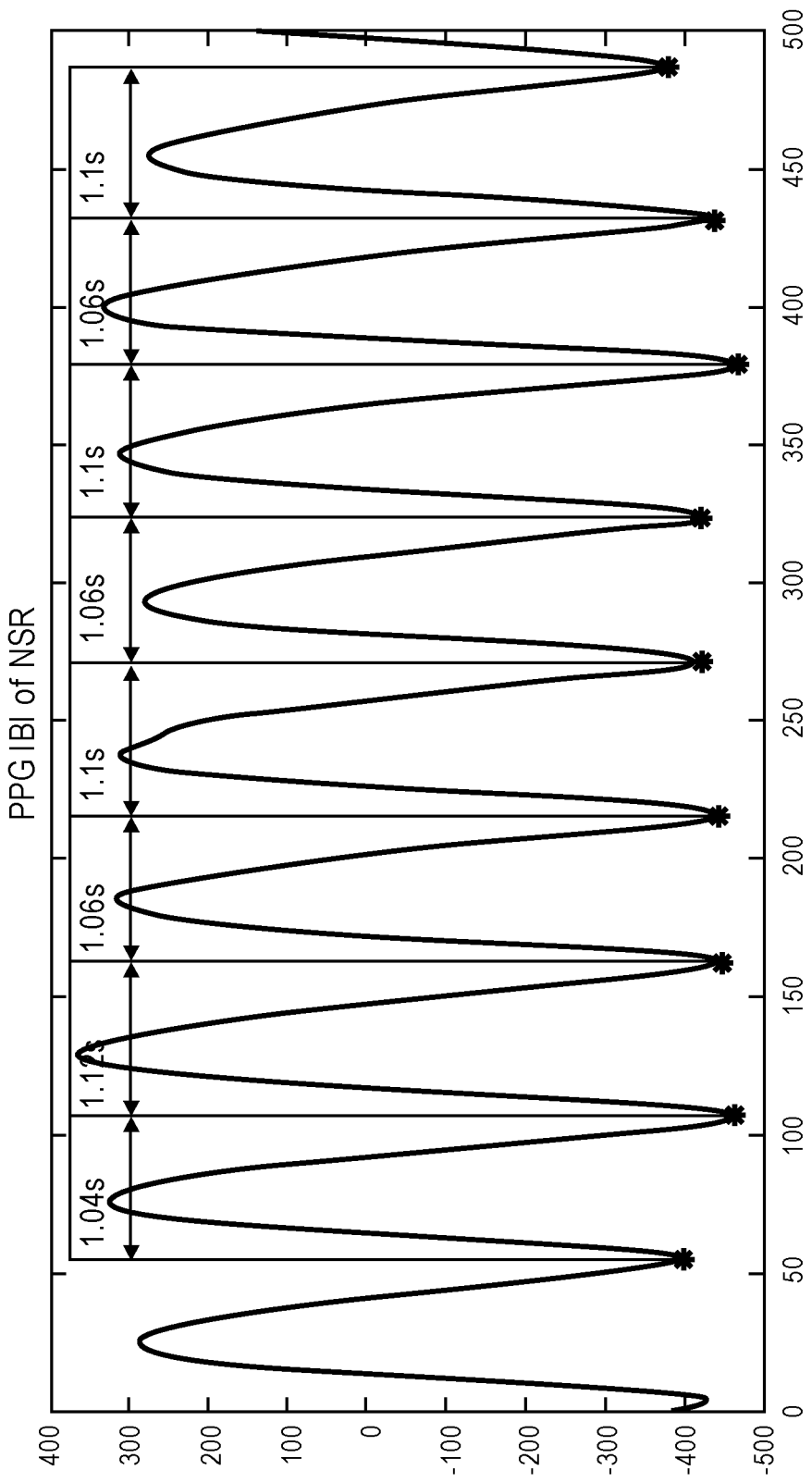
FIG. 5 illustrates exemplary signal waveform of a sequence of PPG signal samples.

Returning to FIG. 3, at 206, the method 200 detects beats in the PPG signal samples. In one embodiment, the method 200 detects the peaks or valleys in the signal waveform of the PPG signal and uses the detected peaks or valleys to indicate the location of a beat in the PPG signal samples. FIG. 5 illustrates exemplary signal waveform of a sequence of PPG signal samples. Referring to FIG. 5, in the present embodiment, the method 200 detects the valleys in the signal waveform to determine the location of a beat or heart beat in the PPG signal samples. Accordingly, the method 200 identifies the boundary of each pulse in the PPG signal samples as a beat.

Returning to FIG. 3, at 208, the method 200 divides the PPG signal samples into PPG signal segments. In one embodiments, the method 200 divides the PPG signal samples into PPG signal segments having a given time duration, such as t number of seconds. For example, each PPG signal segment may be 2 to 15 seconds. In another embodiment, the method 200 divides the PPG signal samples into PPG segments of n number of beats. For example, each PPG signal segment may include 40 to 70 beats.

In embodiments of the present disclosure, the method 200 collects beats for a given time duration to form a PPG signal segment, where the beats in a PPG signal segment may or may not be continuous in time. In other embodiments of the present disclosure, the method 200 collects a given number of beats to form a PPG signal segment, where the beats in a PPG signal segment may or may not be continuous in time. The method 200 may collect some beats in the PPG signal samples, then discard some beats and then resume to collect some other beats to form the PPG signal segment.

At 210, the method 200 extract inter-beat interval features in each PPG signal segment. In particular, the method 200 evaluates the PPG signal segments to analyze the statistical regularity of the distribution of the inter-beat intervals of the PPG beats contained in each PPG signal segment. In this manner, the method 200 can extract inter-beat interval characteristics that are irregularly irregular. In one embodiment, the IBI feature extraction step is performed by the IBI detection module 194 in the detection module 190 of the processor 130 of the user-wearable device 100.

For normal PPG pulses, the time interval between an individual's heart beats varies in a fairly predictable way, due to respiration and other longer-term sympathetic responses. However, when the individual has an arrhythmia, the inter-beat intervals become very irregular due to the abnormal activation patterns present in the tissue, making the intervals distinctly more erratic and less predictable, statistically. The erratic inter-beat intervals can be observed by comparing normal PPG pulses to PPG pulses with arrhythmia.

Figure 6:
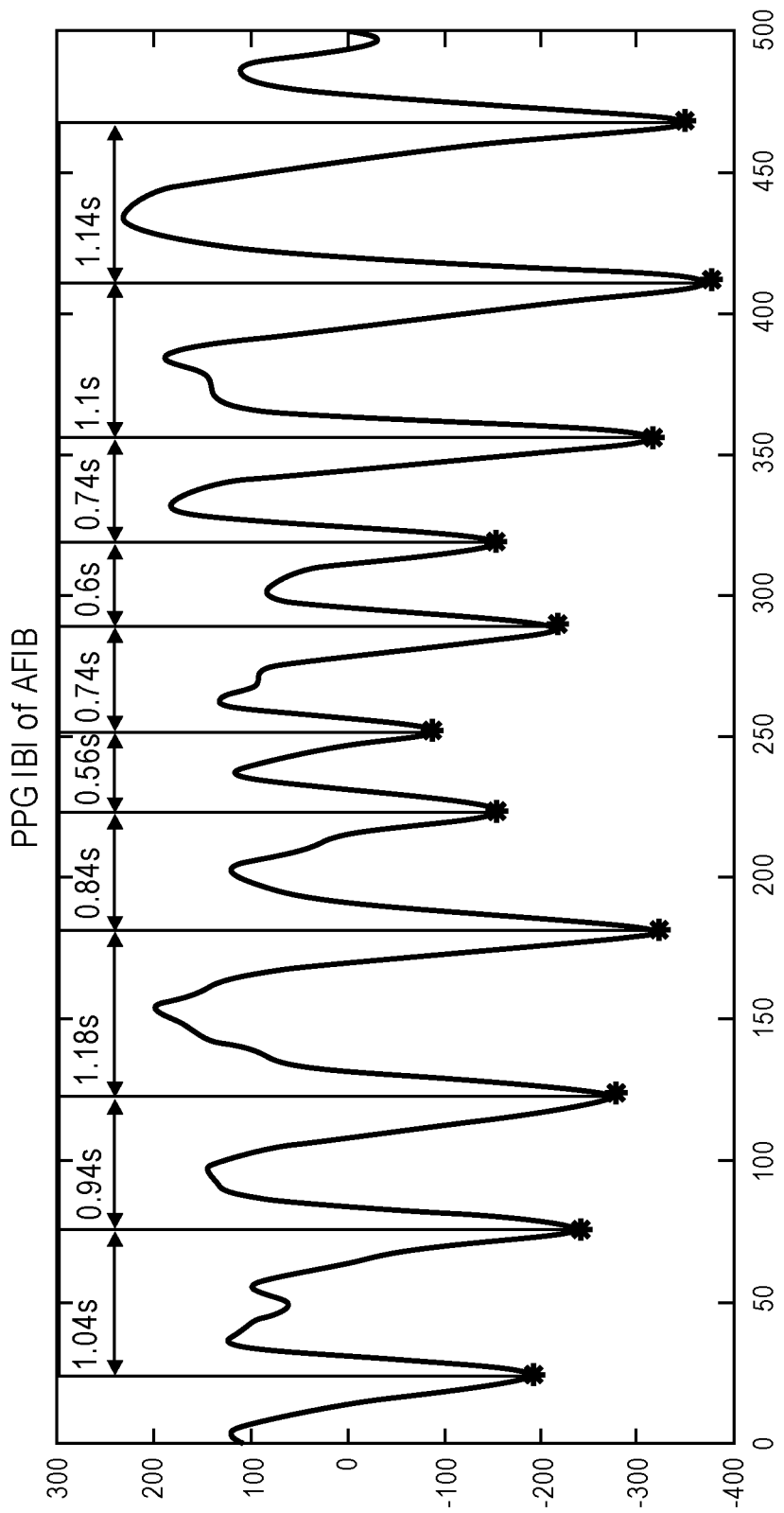
FIG. 6 illustrates exemplary signal waveform of a sequence of PPG signal samples with atrial fibrillation.

In particular, FIG. 5 illustrates PPG signal samples collected from subjects in Normal Sinus Rhythm. The IBI time durations vary from 1.04 seconds to 1.12 seconds. While the IBI time durations vary over the PPG pulses, the IBI time durations are consistent and vary in a predictable manner. FIG. 6 illustrates exemplary signal waveform of a sequence of PPG signal samples with atrial fibrillation. In the case the PPG signal samples present with arrhythmia, the IBI time durations vary widely over the set of PPG pulses. In the present example, the IBI time durations vary from 0.56 seconds to 1.14 seconds. This irregularly irregularity is an indication of arrhythmia or atrial fibrillation.

In embodiments of the present disclosure, the method 200 analyze each PPG signal segment and extracts the 'irregularly irregularity' feature of the IBI in the PPG signals. In some embodiments, the irregularity in the IBI of the PPG signals is characterized using one or more statistical measures of the distribution of the inter-beat interval (IBI) quantity. In some embodiments, the method 200 implements one or more statistical measures to evaluate the IBI time duration. In one example, the statistical measures may include Standard deviation, Skewness, Kurtosis, Information Entropy, Root Mean Square of successive differences (RMSSD) of the IBIs, Turning point ratio, and Multiscale Sample Entropy. The statistical measures are used to extract features of the PPG signal segment where the features may indicate deviation from normal sinus rhythm.

Figure 7:
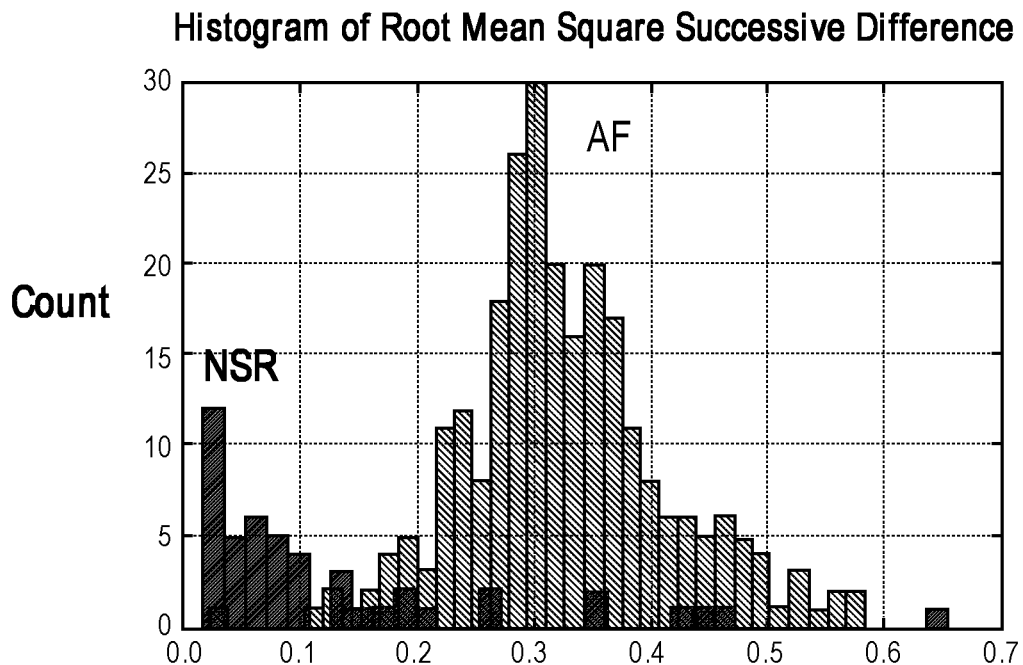
FIG. 7 is a plot illustrating the histogram of the Root Mean Square of successive differences of the IBI of PPG signals with normal sinus rhythm and PPG signals with atrial fibrillation.

FIG. 7 is a plot illustrating the histogram of the Root Mean Square of successive differences of the IBI of PPG signals with normal sinus rhythm and PPG signals with atrial fibrillation. Referring to FIG. 7, by using Root Mean Square of successive differences analysis, PPG signals with normal IBI and PPG signals with abnormal IBI can be readily distinguished.

Figure 8:
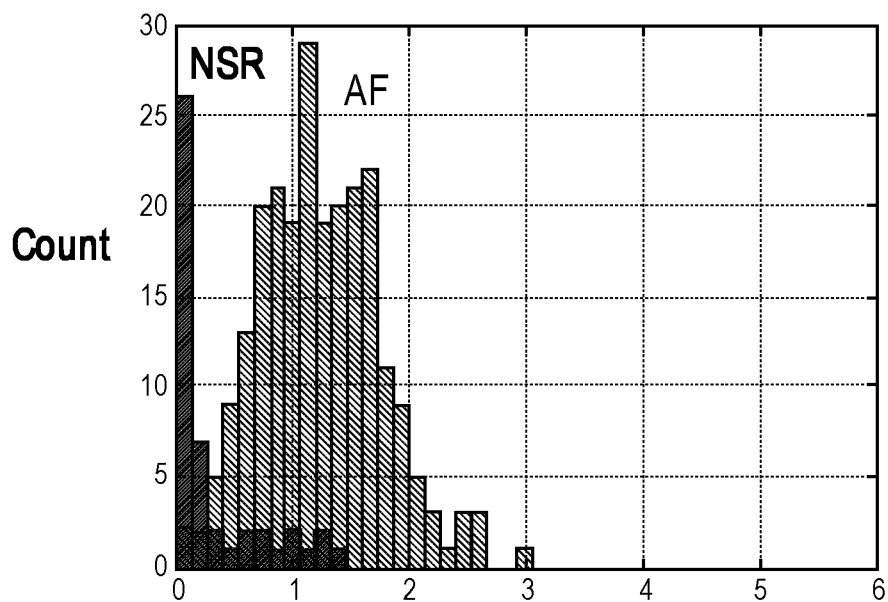
FIG. 8 is a plot illustrating the histogram of the Multiscale Sample Entropy analyses of the IBI of PPG signals with normal sinus rhythm and PPG signals with atrial fibrillation.

FIG. 8 is a plot illustrating the histogram of the Multiscale Sample Entropy analyses of the IBI of PPG signals with normal sinus rhythm and PPG signals with atrial fibrillation. Referring to FIG. 8, by using Multiscale Sample Entropy analysis, PPG signals with normal IBI and PPG signals with abnormal IBI can be readily distinguished.

Returning to FIG. 3, at 212, the method 200 extracts morphology based features in each PPG signal segment. In particular, the method 200 evaluates the PPG signal segments to analyze morphology based features of the PPG beats contained in each PPG signal segment. The morphology based features can include statistical properties, measured features or derived features of the PPG beats in the PPG signal segment. The morphology based features can also include waveform shapes, waveform characteristics, and waveform quality of the PPG beats in the PPG signal segment. In one embodiment, the method 200 analyzes the statistical distribution of morphology characteristics and the similarity between morphology features of adjacent PPG beats extracted from each PPG signal segment. In one embodiment, the morphology feature extraction step is performed by the morphology detection module 196 in the detection module 190 of the processor 130 of the user-wearable device 100.

When in normal sinus rhythm, adjacent PPG beats from a subject in normal sinus rhythm are highly similar in wave shape/morphology, as shown by the PPG pulse waveforms in FIG. 5. But this is not the case for arrhythmias, as shown by the PPG pulse waveforms in FIG. 6. For example, beats that arrive irregularly early typically have not allowed the previous beat's blood to fully disperse in the skin, yielding a DC signal rise, while a similar negative baseline motion can be seen on PPG beats that arrive late. Similarly, since the heart muscle has contracted abnormally, and the blood is ejected differently, the perfusion detected by the PPG waveform can also have a different shape and pressure reflections from the periphery, making up the additive reflected waveforms superimposed on the original pressure pulse. As a result, morphology features can be used as good measures to distinguish normal sinus from cardiac arrhythmias.

Figure 9:
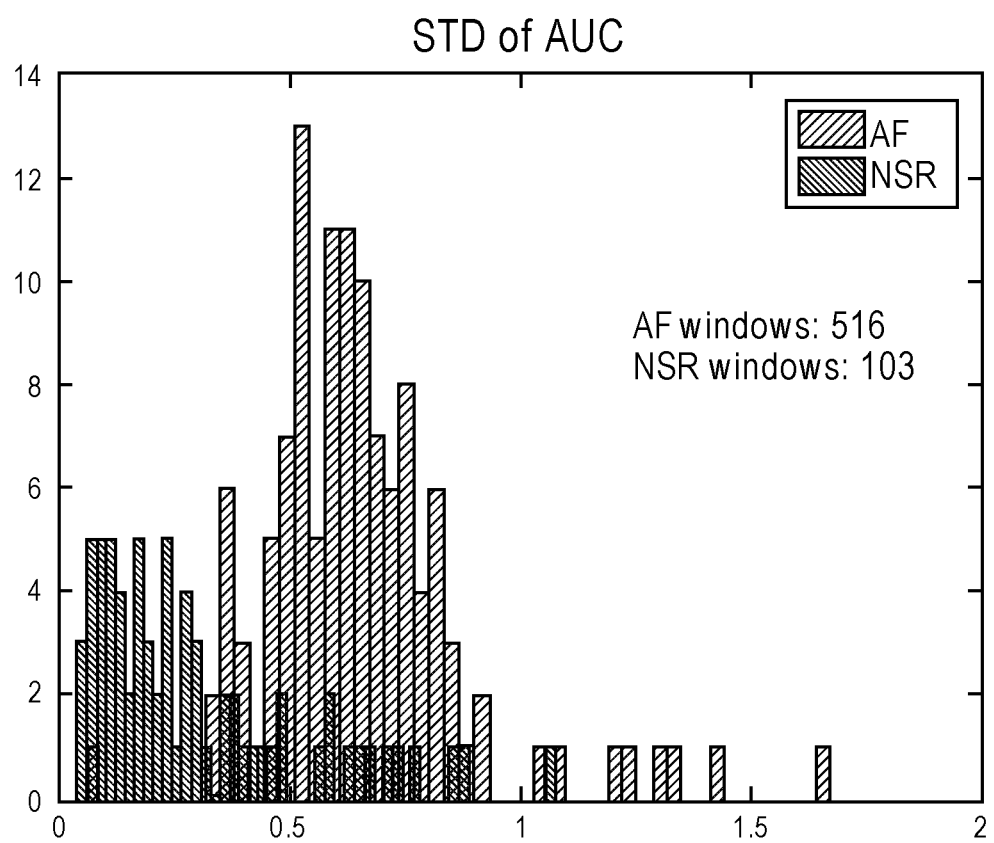
FIG. 9 is a plot illustrating the histograms of standard deviation of the area under the curve for normal sinus and atrial fibrillation.

In embodiments of the present disclosure, the arrhythmia detection method 200 extracts morphology based features including standard deviation of the areas under the curve (AUC) of the PPG beat in a PPG signal segment. For instance, FIG. 9 is a plot illustrating the histograms of standard deviation of the area under the curve for normal sinus and atrial fibrillation. The morphology characteristic difference between the histogram of normal sinus and the histogram of atrial fibrillation can be clearly observed in FIG. 9. The method 200 evaluates the standard deviation of the areas under the curve of the PPG beats in a PPG signal segment to detect for indication of possible cardiac arrhythmia.

In other embodiments, the arrhythmia detection method 200 extracts morphology based features including waveform similarity of adjacent PPG beats in a PPG signal segment. The waveform similarity can be evaluated using cross-correlation or similarity measures. The method 200 evaluates the waveform similarity measures in the PPG beats in a PPG signal segment to detect for indication of possible cardiac arrhythmia.

Figure 10:
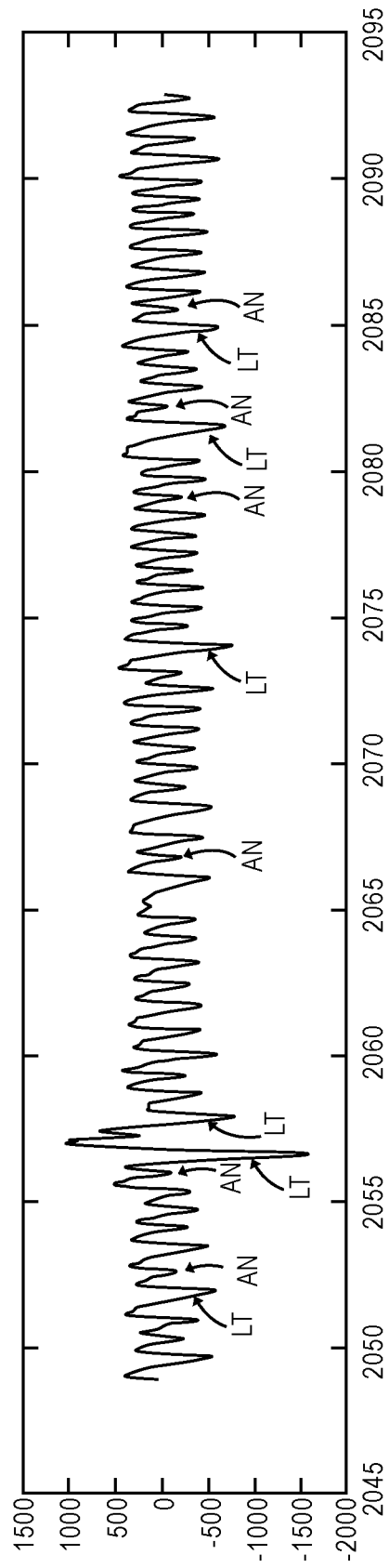
FIG. 10 illustrates exemplary signal waveform of a sequence of PPG signal samples showing long tail features.

In other embodiments, the arrhythmia detection method 200 extracts morphology based features including ratio of PPG beats with long tail in a PPG signal segment. For example, the method 200 detects the percentage occurrence of PPG beats with long tail. In the present description, a PPG beat with long tail refers to a PPG beat waveform with an extended downward slope. That is, the long tail feature refers to an extended downstroke of an arterial pressure waveform. FIG. 10 illustrates exemplary signal waveform of a sequence of PPG signal samples showing long tail features. Referring to FIG. 10, the label LT denotes the PPG pulses with long tail. The method 200 evaluates the PPG beats within a PPG signal segment to detect the number of beats with the long tail feature. The percentage of occurrence of the long tail feature is one morphology based feature that can be used to indicate possible cardiac arrhythmia. In some embodiments, the long tail feature is detected by using pattern recognition technique.

In other embodiments, the arrhythmia detection method 200 extracts morphology based features including ratio of PPG beats with abnormal notches in a PPG signal segment. For example, the method 200 detects the percentage occurrence of PPG beats with abnormal notches. Abnormal notch is different from previously descripted dicrotic notch in that an abnormal notch represents two uncompleted abnormal heart beats, while a dicrotic notch represents one normal heart beat. Referring to FIG. 10, the label AN denotes the PPG pulses with abnormal notches. The method 200 evaluates the PPG beats within a PPG signal segment to detect the number of beats with the abnormal notch feature. The percentage of occurrence of the abnormal notch feature is one morphology based feature that can be used to indicate possible cardiac arrhythmia. In some embodiments, the abnormal notch feature is detected by using pattern recognition technique.

In other embodiments, the arrhythmia detection method 200 extracts morphology based features including the standard deviation of the alternating current (AC) components of the rising edges and standard deviation of the AC components of the falling edges of the PPG beats in a PPG signal segment. A PPG waveform includes an alternating current (AC) component and a direct current (DC) component. The AC component corresponds to variations in blood volume in synchronization with the heart beat. The DC component arises from the optical signals reflected or transmitted by the tissues and is determined by the tissue structure as well as venous and arterial blood volumes. The DC component shows minor changes with respiration. The basic frequency of the AC component varies with the heart rate and is superimposed on the DC baseline. In one embodiment, the method 200 calculates the AC amplitude of the rising edge of a heart beat as the positive area of the $1^{st}$ derivative of PPG waveform and the AC amplitude of the falling edge of the heart beat as the negative area of the $1^{st}$ derivative of the PPG waveform. In an alternate embodiment, PPG alternating current (AC) pulse waveform contour may be characterized by signal samples, systolic peak amplitude, diastolic peak amplitude, 2nd derivative extremes of the pulse waveform. In embodiments of the present disclosure, the method 200 evaluates the standard deviation of the AC components of the PPG beats in a PPG signal segment to detect for indication of possible cardiac arrhythmia.

At 214, the method 200 classifies the PPG signal segments using the extracted IBI features and/or the extracted morphology features associated with each PPG signal segment. The method 200 classifies the PPG signal segment using a machine learning model that was previously trained based on signals and arrhythmia annotations from one or more sets of arrhythmia training data. In one embodiment, the method 200 classifies the PPG signal segments using a combination of IBI features and morphology features. In particular, certain morphology features are indicative of cardiac arrhythmia. Therefore, using a combination of IBI and morphology based features can be instrumental in increasing the likelihood of arrhythmia prediction. In one embodiment, the classification step is performed by the classification module 198 in the detection module 190 of the processor 130 of the user-wearable device 100.

In some embodiments, the method 200 uses a random forest classifier to perform the classification. The random forest is an ensemble method which is constructed by combing several different independent base classifiers/decision trees. Each independent classifier is trained using the sampled dataset with replacement from the original training dataset. The features with maximum information gain are selected to split on. The best split features are identified from a random subset of the available features. This bagging/bootstrap aggregation has the advantage of reduction in overfitting so the model can be generalized to a larger population while reducing the error rate. In one embodiment, to enable implementation on embedded system, the random forest model uses only 3 decision trees and the depth of each tree is 5. In this manner, the method 200 enable real time measurement and prediction of arrhythmia event.

As used herein, the term "machine learning model" refers to classification models that may uses training to provide accurate classifications. In practice, the training of a classification model is carried out on high power computers and the trained model is then deployed on the device where inference using the model is performed. In some embodiments, any machine learning and/or classification techniques may be employed to perform the classification of the PPG features described above. Briefly stated, embodiments of the present disclosure are directed towards arrhythmia detection or event prediction using machine learning that may be incrementally refined based on expert input. In at least one of the various embodiments, data may be provided to a machine learning model that has been trained using a plurality of classifiers (index, labels or annotations) and one or more sets of training data and/or testing data.

At 216, the method 200 generates an event prediction result based on the extracted IBI features and/or the extracted morphology features associated with each PPG signal segment. In one embodiment, the method 200 generates arrhythmias detection result based on the classification of the PPG segments using the IBI features and/or morphology features of the PPG segments.

In some embodiments, in response to detecting that arrhythmia is present, the arrhythmia detection method 200 sends a notification to the user. For example, the notification may be sent via an application on a mobile device and/or the wearable device.

Using the analyses described above, the PPG based arrhythmia detection system takes multiple short discrete segments of PPG signals as input, using the inter-beat intervals features and/or morphology features extracted from these segments and provide the detection result. In this manner, a passive detection system that can be used throughout the user's day is realized.

In some embodiments, the method 200 receives motion information associated with the user-wearable device (218). For example, the motion information may be obtained from a second sensor, such as an inertial measurement sensor or an accelerometer. The method 200 may use the motion information during the PPG signal segmentation step (208) to discard PPG signal samples that are associated with a high degree of motion and therefore may be unreliable. Alternatively, the PPG sensor may be turned off during high motion periods so no PPG signal is available during these periods. Accordingly, in embodiments of the present disclosure, the PPG signal segments thus generated are not necessarily contiguous in time but can be disjointed PPG signal samples. The arrhythmia detection method 200 may operate on short segments of the PPG signal samples, where each segment of PPG signal samples may be discontinuous in time.

In some embodiments, the method 200 receives ECG signals (220). The method 200 may use the ECG signals to adjust the detected beats in the PPG signal segments. In one example, the method 200 uses the ECG signal for information on the heart rate, which can be used to adaptively adjust the decision threshold and the time interval between beats to improve the detection accuracy. It is instructive to note that the method 200 uses the ECG signals for threshold adjustment only and the determination of the present or absence of arrhythmias is made solely using the PPG signals.

In one example, if arrhythmia is present sufficiently in a given period of PPG during stationary conditions, the user may be requested to take an ECG measurement, whose sensor may be co-located on the wearable device. The combination of PPG and ECG measurements can be interpreted for the presence of arrhythmia by a physician or by an ECG analysis algorithm. The determination can then be presented to the user or stored for future cumulative analysis to identify chronic disease trending.

In the PPG-based arrhythmia detection method 200 described above in FIG. 3, the method 200 illustrates the use of a combination of IBI features and morphology based features for arrhythmias detection. While using a combination of IBI features and morphology based features improves the detection accuracy, the PPG-based arrhythmia detection method of the present disclosure can be implemented using only the IBI features or only the morphology based features. IBI features or morphology based features individually provide indication of arrhythmias which can be used as the basis of accurate arrhythmias detection.

Aspects of this disclosure are described herein with reference to flowchart illustrations or block diagrams, in which each block or any combination of blocks may be implemented by computer program instructions. The instructions may be provided to a processor of a general purpose computer, special purpose computer, or other programmable data processing apparatus to effectuate a machine or article of manufacture, and when executed by the processor the instructions create means for implementing the functions, acts or events specified in each block or combination of blocks in the diagrams.

In this regard, each block in the flowchart or block diagrams may correspond to a module, segment, or portion of code that including one or more executable instructions for implementing the specified logical function(s). It should also be noted that, in some alternative implementations, the functionality associated with any block may occur out of the order noted in the figures. For example, two blocks shown in succession may, in fact, be executed substantially concurrently, or blocks may sometimes be executed in reverse order.

A person of ordinary skill in the art will appreciate that aspects of this disclosure may be embodied as a device, system, method or computer program product. Accordingly, aspects of this disclosure, generally referred to herein as circuits, modules, components or systems, may be embodied in hardware, in software (including firmware, resident software, micro-code, etc.), or in any combination of software and hardware, including computer program products embodied in a non-transitory computer-readable medium having computer-readable program code embodied thereon.

The above detailed descriptions are provided to illustrate specific embodiments of the present disclosure and are not intended to be limiting. Numerous modifications and variations within the scope of the present disclosure are possible. The present disclosure is defined by the appended claims.

What is claimed is:

1. A method for event detection in a user-wearable device, comprising:
   receiving, from a first sensor implemented in the user-wearable device, photoplethysmogram (PPG) signals;
   processing, at a processor, the PPG signals to obtain PPG signal samples;
   detecting, at the processor, beats in the PPG signal samples;
   dividing the PPG signal samples into PPG signal segments;
   extracting at least one inter-beat interval (IBI) feature in each PPG signal segment;
   classifying, at the processor, each PPG signal segment using the extracted IBI feature associated with the PPG signal segment and using a machine learning model;
   in response to the classifying, generating, at the processor, an event prediction result for the PPG signal segment based on the extracted IBI feature; and
   displaying the event prediction result at the user-wearable device,
   wherein the event prediction result is indicative of a probability that cardiac arrhythmias is present in a given PPG signal segment.

2. The method of claim 1, further comprising:
   extracting at least one morphology based feature in each PPG signal segment;
   classifying, at the processor, each PPG signal segment using the extracted IBI feature and the extracted morphology based feature associated with the segment and using the machine learning model; and
   in response to the classifying, generating, at the processor, the event prediction result based on the extracted IBI feature and the extracted morphology based feature.

3. The method of claim 1, wherein extracting at least one inter-beat interval (IBI) feature in each PPG signal segment comprises:
   extracting one or more IBI features by analyzing a time duration of the inter-beat intervals of the detected beats in the PPG signal segment using one or more of Standard deviation, Skewness, Kurtosis, Information Entropy, Turning Point Ratio, Root Mean Square of successive differences, and Multiscale Sample Entropy.

4. The method of claim 2, wherein extracting at least one morphology based feature in each PPG signal segment comprises:
   extracting one or more morphology based features by analyzing one or both of a statistical distribution of morphology characteristics and a similarity between morphology features of adjacent beats in each PPG signal segment.

5. The method of claim 4, wherein extracting one or more morphology based features comprises:
   extracting one or more morphology based features by analyzing one or more of a standard deviation of areas under the curve of the detected beat in each PPG signal segment; waveform similarities of adjacent beats in a PPG signal segment; a ratio of PPG beats with long tail in a PPG signal segment; a ratio of PPG beats with abnormal notches in a PPG signal segment; and a standard deviation of the alternating current (AC) component of rising edges and falling edges of the beats in a PPG signal segment.

6. The method of claim 1, wherein dividing the PPG signal samples into PPG signal segments comprises dividing the PPG signal samples into PPG signal segments having a given time duration of t number of seconds.

7. The method of claim 1, wherein dividing the PPG signal samples into PPG signal segments comprises dividing the PPG signal samples into PPG signal segments by number of beats, each segment having n number of beats.

8. The method of claim 1, wherein the PPG signal samples in one or more PPG signal segments comprise PPG signal samples collected over non-continuous time duration.

9. The method of claim 8, further comprising:
   receiving, from a second sensor implemented in the user-wearable device, motion signal indicative of motion activity at the user-wearable device;
   in response to the motion signal, removing PPG signal samples associated with a high degree of motion activity; and
   dividing the PPG signal samples into PPG signal segments by dividing the remaining PPG signal samples, the remaining PPG data samples being collected over a non-continuous time duration.

10. The method of claim 9, wherein the first sensor comprises a photoplethysmogram (PPG) sensor and the second sensor comprises an accelerometer.

11. The method of claim 1, further comprising:
    receiving at the processor, electrocardiogram (ECG) signals;
    adjusting the PPG signal samples in each PPG signal segment using the ECG signals; and
    adjusting a decision threshold during classifying to increase a detection accuracy.

12. The method of claim 1, further comprising:
    in response to the prediction result indicating a high probability that an event is present in a given PPG signal segment, providing a notification on the user-wearable device.

13. The method of claim 1, wherein processing, at a processor, the PPG signals to obtain PPG signal samples comprises processing, at a processor implemented in the user-wearable device, the PPG signals to obtain PPG signal samples.

14. The method of claim 1, wherein processing, at a processor, the PPG signals to obtain PPG signal samples comprises processing, at a processor implemented in a mobile device in communication with the user-wearable device, the PPG signals to obtain PPG signal samples.

15. The method of claim 1, wherein processing, at a processor, the PPG signals to obtain PPG signal samples comprises processing, at a processor implemented in a cloud server in communication with the user-wearable device, the PPG signals to obtain PPG signal samples.

16. A method for event detection in a user-wearable device, comprising:
    receiving, from a first sensor implemented in the user-wearable device, photoplethysmogram (PPG) signals;
    processing, at a processor, the PPG signals to obtain PPG signal samples;
    detecting, at the processor, beats in the PPG signal samples;
    dividing the PPG signal samples into PPG signal segments;
    extracting at least one morphology based feature in each PPG signal segment, the morphology based features being associated with statistical characteristics of the PPG signal samples or waveform characteristics of the PPG signal samples;
    classifying, at the processor, each PPG signal segment using the extracted morphology based feature associated with the PPG signal segment and using a machine learning model;

in response to the classifying, generating, at the processor, an event prediction result based on the extracted morphology based feature; and displaying the event prediction result at the user-wearable device, wherein the event prediction result is indicative of a probability that cardiac arrhythmias is present in the PPG signal segment.

17. The method of claim 16, wherein extracting at least one morphology based feature in each PPG signal segment comprises:

extracting one or more morphology based features by analyzing one or both of a statistical distribution of morphology characteristics and a similarity between morphology features of adjacent beats in each PPG signal segment.

18. The method of claim 17, wherein extracting one or more morphology based features comprises:

extracting one or more morphology based features by analyzing one or more of a standard deviation of areas under the curve of the detected beat in each PPG signal segment; waveform similarities of adjacent beats in a PPG signal segment; a ratio of PPG beats with long tail in a PPG signal segment; a ratio of PPG beats with abnormal notches in a PPG signal segment; and a standard deviation of the alternating current (AC) component of rising edges of the PPG beats and a standard deviation of the AC component of falling edges of the PPG beats in a PPG signal segment.

19. An apparatus, comprising:

a sensor module comprising a first sensor configured to measure photoplethysmogram (PPG) signals; and a processor comprising:

a data processing module configured to process the PPG signals to obtain PPG signal samples, to detect beats in the PPG signal samples, and to divide the PPG signal samples into PPG signal segments;

an inter-beat interval detection module configured to extract at least one inter-beat interval (IBI) feature in each PPG signal segment;

a morphology detection module configured to extract at least one morphology based feature in each PPG signal segment; and a classification module configured to classify each PPG signal segment using the extracted IBI feature and the extracted morphology based feature associated with the segment and using a machine learning model, the classification module further configured to generate an event prediction result based on the extracted IBI feature and the extracted morphology based feature, wherein the event prediction result is indicative of a probability that cardiac arrhythmias is present in the PPG signal segment.

20. The apparatus of claim 19, wherein the inter-beat interval detection module is configured to extract one or more IBI features by analyzing a time duration of the inter-beat intervals of the detected beats in the PPG signal segment using one or more of Standard deviation, Skewness, Kurtosis, Information Entropy, Turning Point Ratio, Root Mean Square of successive differences, and Multiscale Sample Entropy.

21. The apparatus of claim 19, wherein the morphology detection module is configured to extract one or more morphology based features by analyzing one or both of a statistical distribution of morphology characteristics and a similarity between morphology features of adjacent beats in each PPG signal segment.

22. The apparatus of claim 21, wherein the morphology detection module is configured to extract one or more morphology based features by analyzing one or more of a standard deviation of areas under the curve of the detected beat in each PPG signal segment; waveform similarities of adjacent beats in a PPG signal segment; a ratio of PPG beats with long tail in a PPG signal segment; a ratio of PPG beats with abnormal notches in a PPG signal segment; and a standard deviation of the alternating current (AC) component of rising edges and falling edges of the beats in a PPG signal segment.

* * * * *